US010467463B2

(12) United States Patent
Kim et al.

(10) Patent No.: US 10,467,463 B2
(45) Date of Patent: Nov. 5, 2019

(54) PERSONALIZED EXERCISE SERVICE PROVIDING METHOD AND APPARATUS THEREOF

(71) Applicant: Electronics and Telecommunications Research Institute, Daejeon (KR)

(72) Inventors: Kye-Kyung Kim, Daejeon (KR); Sang-Seung Kang, Daejeon (KR); Su-Young Chi, Daejeon (KR); Jae-Hong Kim, Daejeon (KR); Sung-Woong Shin, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 708 days.

(21) Appl. No.: 15/081,213

(22) Filed: Mar. 25, 2016

(65) Prior Publication Data
US 2016/0279476 A1 Sep. 29, 2016

(30) Foreign Application Priority Data

Mar. 25, 2015 (KR) ........................ 10-2015-0041599

(51) Int. Cl.
*G16H 20/30* (2018.01)
*G06K 9/00* (2006.01)

(52) U.S. Cl.
CPC ......... *G06K 9/00369* (2013.01); *G16H 20/30* (2018.01); *G06T 2207/30221* (2013.01)

(58) Field of Classification Search
CPC .............. G09B 19/003; G09B 19/0038; G06K 9/00369; G16H 20/30; G06T 2207/30221
USPC ....................................................... 434/247
See application file for complete search history.

(56) References Cited

U.S. PATENT DOCUMENTS

2006/0120569 A1 6/2006 Kim et al.
2008/0086318 A1* 4/2008 Gilley ................... G06Q 10/06
   705/319
2008/0096726 A1* 4/2008 Riley ................. A63B 24/0006
   482/8

(Continued)

FOREIGN PATENT DOCUMENTS

KR 1020060063621 A 6/2006
KR 1020110013765 A 2/2011

(Continued)

OTHER PUBLICATIONS

A. C. Gallagher, A. C. Blose and T. Chen, "Jointly estimating demographics and height with a calibrated camera," 2009 IEEE 12th International Conference on Computer Vision, Kyoto, 2009, pp. 1187-1194. doi: 10.1109/ICCV.2009.5459340 URL: <http://ieeexplore.ieee.org/stamp/stamp.jsp?tp=&arnumber=5459340 &isnumber=5459144>.*

*Primary Examiner* — Robert P Bullington
(74) *Attorney, Agent, or Firm* — William Park & Associates Ltd.

(57) ABSTRACT

Disclosed are a personalized exercise service providing method and an apparatus thereof. A personalized exercise service providing apparatus according to an example includes a user class identifier configured to identify user class of a user; an exercise data acquirer configured to acquire exercise data of the user; and a model generator configured to generate a personalized exercise model of the user based on a standard exercise model corresponding to the determined user class and the acquired exercise data of the user to provide the most effective exercise model to each user through user recognition.

16 Claims, 8 Drawing Sheets

(56) References Cited

U.S. PATENT DOCUMENTS

| | | | |
|---|---|---|---|
| 2013/0072353 A1* | 3/2013 | Alessandri | A63B 21/062 482/8 |
| 2013/0100269 A1* | 4/2013 | Tashiro | G06F 19/3418 348/77 |
| 2014/0079295 A1 | 3/2014 | Yoon et al. | |

FOREIGN PATENT DOCUMENTS

| | | |
|---|---|---|
| KR | 1020120096286 A | 8/2012 |
| KR | 1020140036803 A | 3/2014 |

* cited by examiner

FIG. 2

| Sex | Age | Body type | Exercise time |
|---|---|---|---|
| Male | Twenties | Skinny | 1hour |
| | Twenties | Fat | 2hours |
| | Twenties | Standard | 1hour |
| | ... | ... | ... |
| | Sixties | Skinny | 2hours |
| | Sixties | Fat | 1hour |
| | Sixties | Standard | 2hours |

PERSONALIZED EXERCISE SERVICE PROVIDING METHOD AND APPARATUS THEREOF

CROSS REFERENCE TO RELATED APPLICATION(S)

This application claims the benefit under 35 USC § 119(a) of Korean Patent Application No. 10-2015-0041599 filed on Mar. 25, 2015 in the Korean Intellectual Property Office, the entire disclosure of which is incorporated herein by reference for all purposes.

BACKGROUND

1. Field

The following description relates to a personalized exercise service providing method and an apparatus thereof.

2. Description of Related Art

Recently, outdoor exercises have changed to indoor exercises in accordance with development of exercise equipment. Technologies have been also developed to correct exercise postures by analyzing exercise motions of users in an outdoor environment-reflected virtual reality space and/or provide personalized exercises by determining users' biological properties.

A personalized service has been applied on sports fields in addition to entertainment fields, for example, such as music and advertisement to provide personalized contents.

Interests in health and more particularly, demands on personalized exercise services have been increased in an aging society. However, technologies to satisfy such demands are practically not developed much.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A personalized exercise service providing apparatus according to an example may be provided.

A personalized exercise service providing apparatus according to an example may provide a proper personalized exercise model based on sex, age, and body type of a user.

A personalized exercise service providing apparatus according to an example may provide exercise equipment information proper to a user's body type.

According to one general aspect, a personalized exercise service providing apparatus may include a user class identifier configured to identify user class of a user; an exercise data acquirer configured to acquire exercise data of the user; and a model generator configured to generate a personalized exercise model of the user based on a standard exercise model corresponding to the determined user class and the acquired exercise data of the user.

The user class may be classified based on at least one of sex, age, and body type of the user.

The apparatus may further include an image processor configured to recognize an image that is obtained by a visual sensor, wherein the user class identifier may identify the user class based on image recognition result received from the image processor and pre-established database.

The pre-established database may include at least one of feature vector for each user class and information of body feature points for each user class.

The image processor may detect a face region of the user from an image that is obtained by a first visual sensor, extract at least one of feature vector for sex identification and feature vector for age identification from the detected face region, and provide the extracted feature vector to the user class identifier as the image recognition result. The user class identifier may identify at least one of sex and age of the user based on the image recognition result received from the image processor.

The image processor may detect a body region of the user from an image that is obtained by a second visual sensor, extract body feature points from the detected body region, and provide information of the extracted body feature points to the user class identifier as the image recognition result. The user class identifier may identify body type of the user based on the image recognition result received from the image processor.

The apparatus may further include an equipment controller configured to control exercise equipment based on the identified body type of the user or provide exercise equipment information to the user.

The apparatus may further include an image processor configured to recognize an image that is obtained by a visual sensor, wherein the exercise data acquirer may acquire the exercise data of the user by analyzing the image recognition result received from the image processor.

The model generator may compare exercise data of the standard exercise model corresponding to the user class with the acquired exercise data to generate the personalized exercise model comprising the difference thereof.

The model generator may build database for generating exercise models corresponding to each user class by using exercise data of users and generate the standard exercise model corresponding to each user class based on the built database for generating exercise models.

According to another general aspect, a personalized exercise service providing method may include determining a user class of a user; acquiring exercise data of the user; and generating a personalized exercise model of the user based on a standard exercise model corresponding to the determined user class and the acquired exercise data of the user.

The method may further include acquiring an image of the user; recognizing the image; and identifying the user class based on the image recognition result and pre-established database.

The recognizing the image may include detecting a face region of the user from an image that is obtained by a first visual sensor and extracting at least one of feature vector for sex identification and feature vector for age identification from the detected face region. Here, the identifying the user class may include identifying at least one of sex and age of the user based on the extracted feature vector.

The recognizing the image may include detecting a body region of the user from an image that is obtained by a second visual sensor and extracting body feature points from the detected body region. Here, the identifying the user class may include identifying body type of the user based on information of the extracted body feature points.

The method may further include controlling exercise equipment based on the identified body type of the user or providing exercise equipment information to the user.

The acquiring exercise data of the user may include acquiring an image of the user; recognizing the image of the user; and acquiring the exercise data of the user by analyzing the image recognition result.

The generating a personalized exercise model may include comparing exercise data of the standard exercise model corresponding to the user class with the acquired exercise data to generate the personalized exercise model comprising the difference thereof.

The method may further include building database for generating exercise models corresponding to each user class by using exercise data of users; and generating the standard exercise model corresponding to each user class based on the built database for generating exercise models.

The personalized exercise service providing method and apparatus according to an example may provide the most effective exercise model to user through user recognition to optimize exercise effect of users.

Other features and aspects will be apparent from the following detailed description, the drawings, and the claims.

BRIEF DESCRIPTION OF THE DRAWINGS

FIG. 2 is an example of a standard exercise model.

Figure 1:
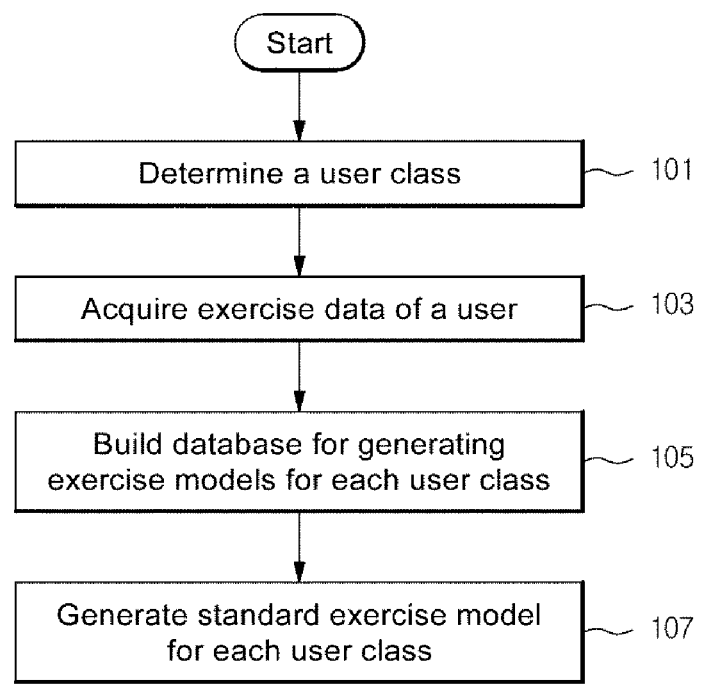
FIG. 1 is a flowchart illustrating an example of a method for generating a standard exercise model.

Throughout the drawings and the detailed description, unless otherwise described or provided, the same drawing reference numerals refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure is thorough, complete, and conveys the full scope of the disclosure to one of ordinary skill in the art.

It will be understood that, although the terms "first," "second," "third," "fourth" etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. Similarly, when it is described that a method includes series of steps, a sequence of the steps is not a sequence in which the steps should be performed in the sequence, an arbitrary technical step may be omitted and/or another arbitrary step, which is not disclosed herein, may be added to the method.

Disclosed is to provide personalized exercise services based on sex, age and body type.

It is assumed that a standard exercise model is generated for each user class which is classified based on sex, age and body type.

When a user in a particular user class exercises, a personalized exercise model of the user may be provided based on the standard exercise model of that particular user class and exercise data acquired from the user.

A method for generating a standard exercise model will be explained with reference to FIG. 1 to FIG. 6 and a personalized exercise model providing method will be explained with reference to FIG. 7.

FIG. 1 is a flowchart illustrating an example of a method for generating a standard exercise model. At least one step of the method in FIG. 1 can be omitted.

In step 101, a personalized exercise service providing apparatus according to an example may determine a user class of a user. The user class may be determined based on at least one of sex, age, and body type of the user. The personalized exercise service providing apparatus may include a user class list including at least one identification item of sex, age and body type. The user class list may be generated automatically or inputted by a user or an operator during identifying the user.

In step 103, the personalized exercise service providing apparatus may acquire exercise data of the user, for example, such as exercise posture, the exercise pattern, the exercise environment, the exercise time and types of exercise. The exercise data may be acquired continuously or periodically.

In step 105, the personalized exercise service providing apparatus may establish database for generating exercise models corresponding to the user class. The database for generating exercise models corresponding to the user class may be established by mapping the user's exercise data acquired in step 103 to the user class to which the user belongs and storing the result.

When the database for generating exercise models corresponding to the user class is already established, the personalized exercise service providing apparatus may update the database for generating exercise models of the corresponding user class using the user's exercise data acquired in step 103. The database for generating exercise models may be updated continuously or periodically.

In step 107, the personalized exercise service providing apparatus may generate a standard exercise model corresponding to each user class. For example, the personalized exercise service providing apparatus may generate a standard exercise model for each class based on the database for generating exercise models established for each user class. The standard exercise model may include an average value of the exercise data for each class. The standard exercise model may be updated when the database for generating exercise models is updated.

FIG. 2 is an example of a standard exercise model. FIG. 2 is an example of a standard exercise model of each user class which is based on sex, age and body type. The example of the standard exercise model includes data of exercise time for convenience of description. Here, the exercise time may be average exercise time of users in each user class.

Figure 3:
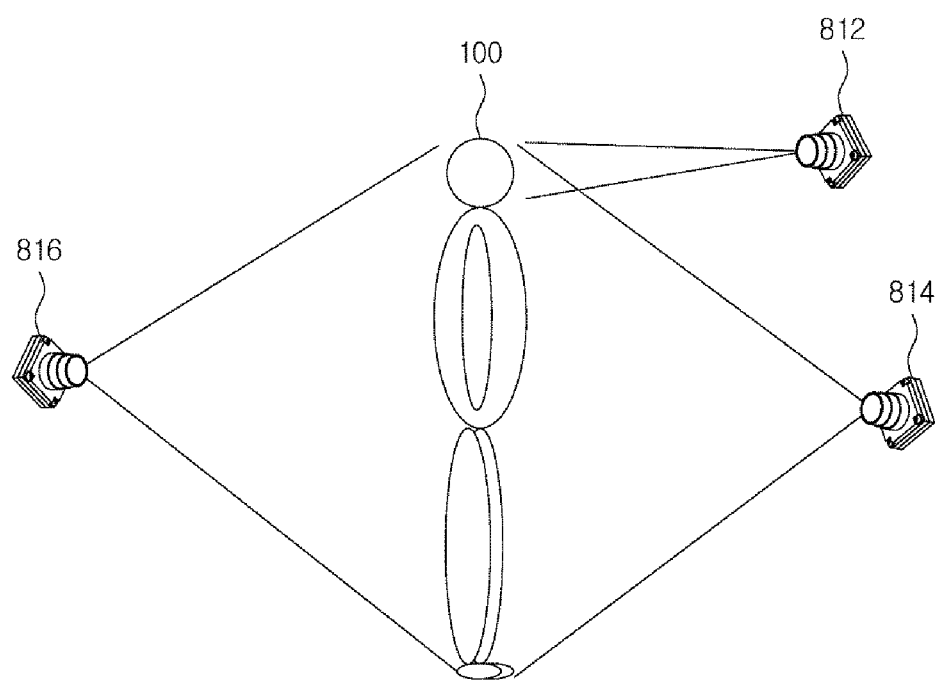
FIG. 3 is a diagram illustrating an example of environment for identifying a user class and acquiring exercise data.

FIG. 3 is a diagram illustrating an example of environment for identifying a user class and acquiring exercise data.

A user 100 may be positioned in front of exercise equipment and one or more visual sensors 812, 814, 816 may be arranged around the user 100. The visual sensors 812, 814, 816 may take photos of the user to generate images. The images may be used for image recognition to determine a user class based thereon.

The user class may be determined based on at least one of sex, age, and body type of a user. A method for identifying sex and age of a user will be explained with reference to FIG. 4 and a method for identifying body type of a user will be explained with reference to FIG. 5.

Figure 4:
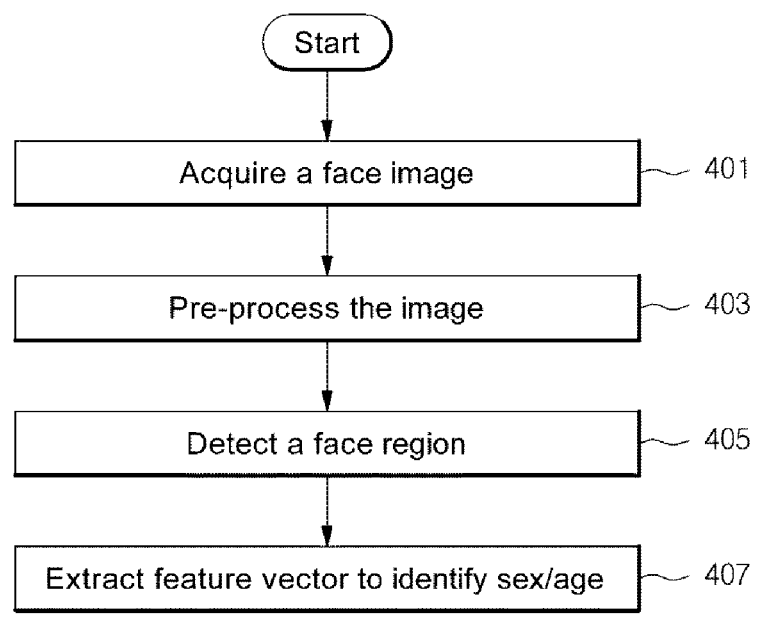
FIG. 4 is a flowchart illustrating an example of a method for identifying sex and age of a user.

FIG. 4 is a flowchart illustrating an example of a method for identifying sex and age of a user. At least one step of the method in FIG. 4 can be omitted.

In step 401, a personalized exercise service providing apparatus may acquire an image of a user. For example, a face image of the user may be obtained by the first visual sensor 812 illustrated in FIG. 2. The first visual sensor 812 may be arranged in front of the user.

In step 403, the personalized exercise service providing apparatus may pre-process the face image. For example, the personalized exercise service providing apparatus may pre-process the face image to minimize impact from background and lighting.

In step 405, the personalized exercise service providing apparatus may detect a face region from the pre-processed image using various face region detection algorithms. The personalized exercise service providing apparatus may normalize size of the face region into a predetermined size.

In step 407, the personalized exercise service providing apparatus may extract feature vector for identifying sex/age from the detected face region. For example, the personalized exercise service providing apparatus may extract face feature points proper for sex and age recognition and acquire face feature vector from each extracted face feature points. The face feature points may be detected from, for example, eyes, nose, mouth, ears and facial contour. The personalized exercise service providing apparatus may generate new face feature points from the extracted face feature points through interpolation. New face feature vector may be acquired from the generated new face feature points.

The personalized exercise service providing apparatus may compare the acquired face feature vector(or new face feature vector) with pre-learned face feature vector to identify sex and age of the user. For example, the personalized exercise service providing apparatus may identify sex and age of a current user based on the database which stores pre-learned face feature vector corresponding to sex and age.

Figure 5:
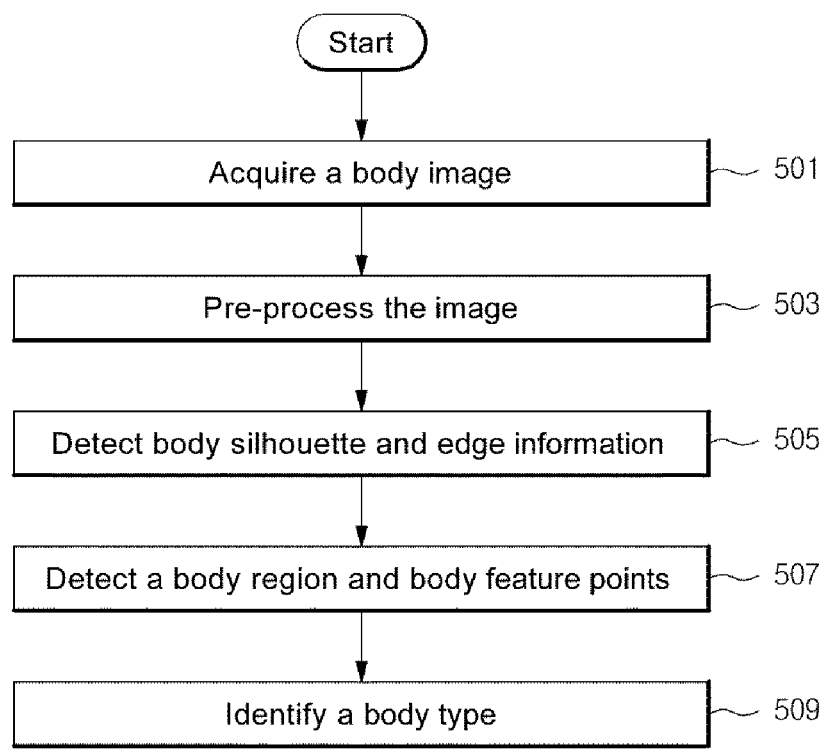
FIG. 5 is a flowchart illustrating an example of a method for identifying body type of a user.

FIG. 5 is a flowchart illustrating an example of a method for identifying body type of a user. At least one step of the method in FIG. 5 can be omitted.

In step 501, a personalized exercise service providing apparatus may acquire a body image of a user. For example, the body image of a user may be obtained by the second visual sensor 814 illustrated in FIG. 3. The second visual sensor 814 may be arranged in front of the user. The second visual sensor 814 may be more than one. In this case, the second visual sensors 814 may be arranged evenly around the user.

In step 503, the personalized exercise service providing apparatus may pre-process the body image. For example, the personalized exercise service providing apparatus may pre-process the body image to minimize impact from background and lighting.

In step 505, the personalized exercise service providing apparatus may detect body silhouette and edge information from the pre-processed image.

Figure 6:
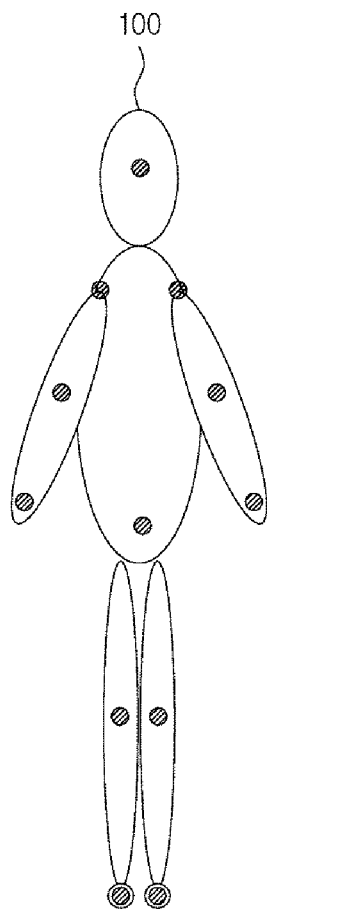
FIG. 6 is diagrams illustrating examples of body feature points.
Figure 6:
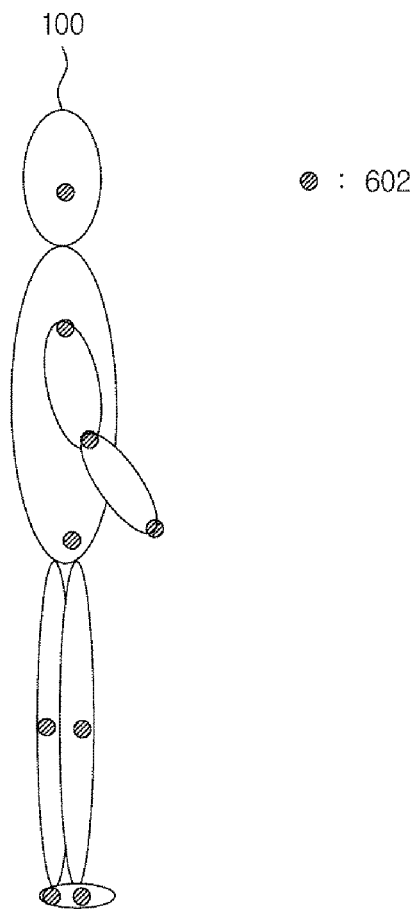

In step 507, the personalized exercise service providing apparatus may detect a body region from the detected body silhouette and edge information to detect body feature points. For example, the body feature points may be detected from at least one of shoulders, arms, legs and joints of a user. Examples of the body feature points are illustrated in FIG. 6. Referring to FIG. 6, one or more body feature points 602 may be detected from the user.

In step 509, the personalized exercise service providing apparatus may identify a body type of the user based on the detected body feature points. Identifying a body type of the user may be identifying physical features, for example, such as height, arm length and leg length.

Figure 7:
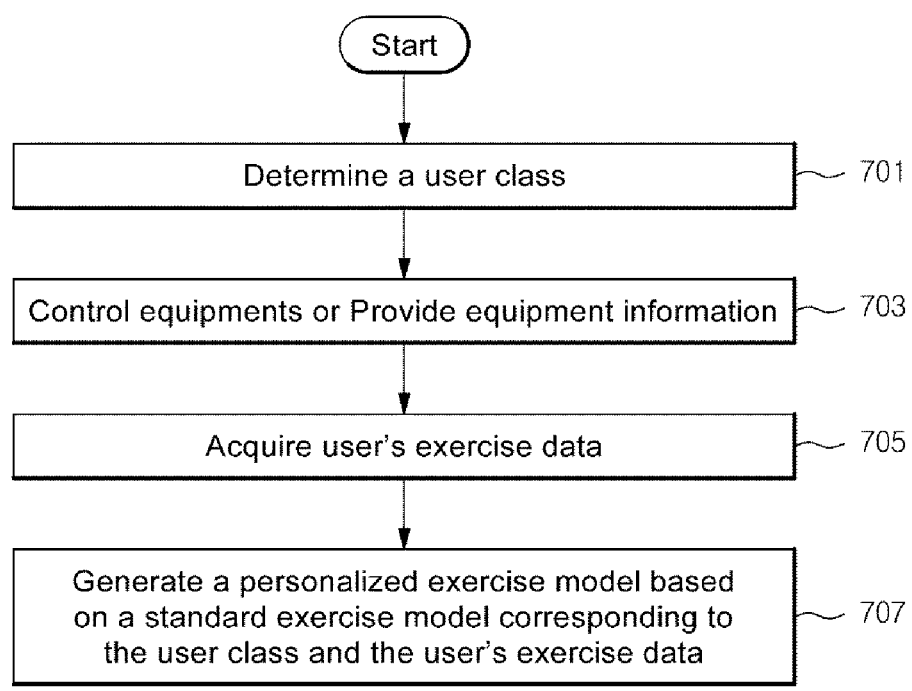
FIG. 7 is a flowchart illustrating an example of a method for generating a standard exercise model.

FIG. 7 is a flowchart illustrating an example of a method for generating a standard exercise model. At least one step of the method in FIG. 7 can be omitted.

In step 701, the personalized exercise service providing apparatus may determine a user class of a user. The user class may be determined based on at least one of sex, age, and body type of a user as in the description above explained with reference to FIG. 1 to FIG. 6.

The personalized exercise service providing apparatus may extract information to identify at least one of sex, age and body type and identify a class of the user based on the extracted information. Description of a method for determining a user class will be omitted since it is the same as in the description above explained with reference to FIG. 1 to FIG. 6.

In step 703, the personalized exercise service providing apparatus may control exercise equipment to be proper to the body type of the user or provide exercise equipment information to set exercise equipment properly based on body type of the user. For example, the personalized exercise service providing apparatus may control exercise equipment to fix with the user's body by considering arm length and leg length of the user. For example, the personalized exercise service providing apparatus may also provide exercise equipment information for the user to control exercise equipment to fit to his/her body. Thus, the user may select desired exercises and equipment and do exercise in a right posture based on the exercise equipment information.

In step 705, the personalized exercise service providing apparatus may acquire user's exercise data.

As described with reference to FIG. 1, the exercise data may include at least one exercise posture, the exercise pattern, the exercise environment, the exercise time and types of exercise. The exercise data may be acquired continuously or periodically. The user's exercise data may be acquired from the image that is obtained by the third visual sensor 816 illustrated in FIG. 3. The third visual sensor 816 may be arranged in front of the user. One or more of the third visual sensors 816 may be used. In this case, these third visual sensors 816 may be arranged evenly around the user. The exercise data acquired in step 705 may be used to establish or update the database for generating exercise model corresponding to each user class.

In step 707, the personalized exercise service providing apparatus may generate a personalized exercise model of the user based on a standard exercise model corresponding to the user class to which the user belongs and the user's exercise data.

The personalized exercise model may include information about difference between the exercise data of the standard exercise model corresponding to the user class to which the user belongs and the exercise data acquired from the current user. For example, when exercise time in the exercise data of the standard exercise model corresponding to the user class to which a current user belongs is 2 hours and exercise time in exercise data acquired from the current user is 1.5 hours, information for requiring 30 more minutes of exercise may be included in the personalized exercise model. For example, when exercise posture in the exercise data of the standard exercise model corresponding to the user class to which a current user belongs is not identical to exercise posture in exercise data acquired from the current user, information for requiring a corrected exercise posture may be included in the personalized exercise model.

The personalized exercise model may include information about at least one of exercise posture, the exercise pattern, the exercise environment, the exercise time, types of exercise and exercise equipment.

The personalized exercise model may be used to educate a corresponding user or other users or to provide exercise models proper to other users.

Figure 8:
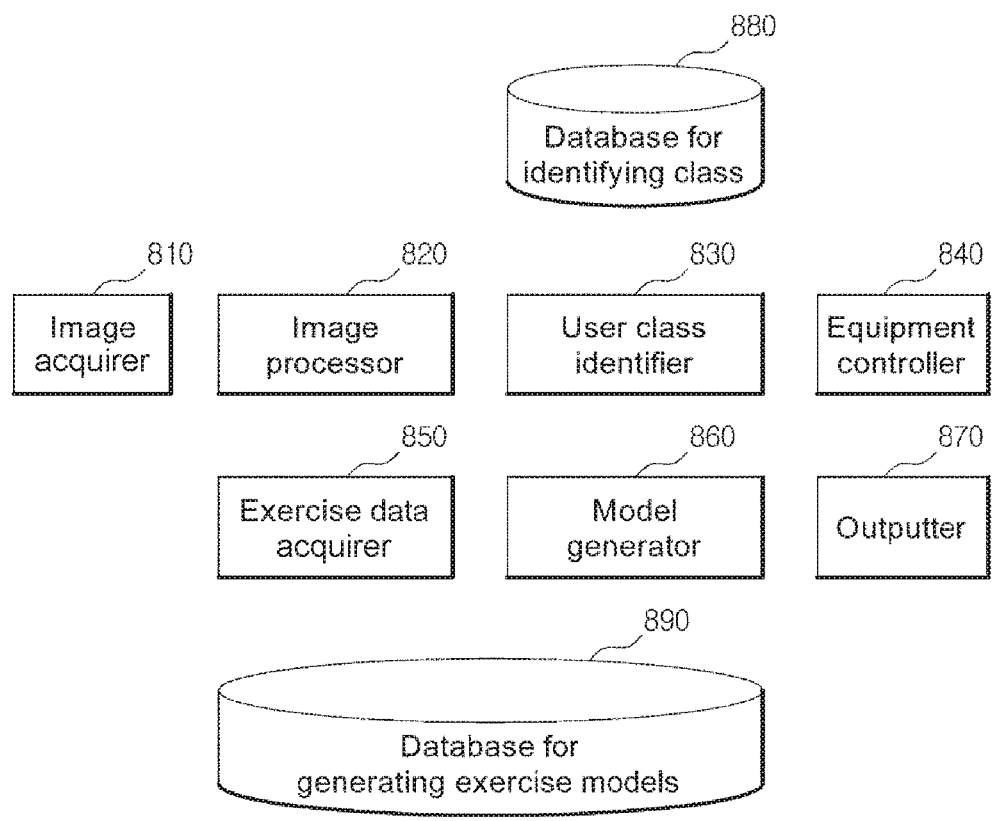
FIG. 8 is a diagram illustrating an example of a personalized exercise service providing apparatus.

FIG. 8 is a diagram illustrating an example of a personalized exercise service providing apparatus.

Referring to FIG. 8, a personalized exercise service providing apparatus may include an image acquirer 810, an image processor 820, a user class identifier 830, an equipment controller 840, an exercise data acquirer 850, a model generator 860, an outputter 870, a database for identifying class 880 and a database for generating exercise models 890. At least one of the elements can be omitted.

The image acquirer 810 may include at least one visual sensor. The image acquirer 810 may include a first visual sensor to take a user's face and a second visual sensor and a third visual sensor to take a user's body.

The image processor 820 may perform image recognition of the image received from the image acquirer.

The image processor 820 may detect a user's face region from the image that is obtained by the first visual sensor. The image processor 820 may extract at least one of feature vector for sex identification and feature vector for age identification from the detected face region and provide the extracted feature vector to the user class identifier 830 as image recognition result.

The image processor 820 may detect a user's body region from the image that is obtained by the second visual sensor. The image processor 820 may extract body feature points from the detected body region and provide information of the extracted body feature points to the user class identifier 830 as image recognition result.

The image processor 820 may detect a user's body region from the image that is obtained by the third visual sensor. The image processor 820 may extract body feature points from the detected body region and provide information of the extracted body feature points to the exercise data acquirer 850 as image recognition result.

The user class identifier 830 may determine a user class of the user. The user class identifier 830 may determine a user class of the user based on the image recognition result received from the image processor 820 and information stored in the database for identifying class 880. The user class may be classified based on at least one of sex, age, and body type of a user.

The image recognition result may include at least one of feature vector and information of body feature points of the user. The database for identifying class 880 may include at least one of feature vector for each user class and information of body feature points for each user class.

The equipment controller 840 may control exercise equipment based on body type information of the user received from the user class identifier 830 or provide exercise equipment information to the user through the outputter 870.

The exercise data acquirer 850 may acquire user's exercise data based on the image recognition result received from the image processor 820. For example, the exercise data acquirer 850 may acquire information of user's exercise posture based on information of the body feature points received from the image processor 820. For example, the exercise data acquirer 850 may receive exercise environment information, for example, such as media contents information from an external device. The exercise environment information may be used to analyze how environment factors affect to user's exercise. The exercise environment information may be used to provide optimal exercise environment to the user.

The model generator 860 may build the database for generating exercise models 890 for each user class by utilizing exercise data of at least one user. The model generator 860 may generate standard exercise model corresponding to each user class based on the database for generating exercise models 890. The standard exercise model may include average values of the exercise data acquired from users in the corresponding class.

The model generator 860 may generate a personalized exercise model of the user based on the standard exercise model of the user class and the user's exercise data. For example, the model generator 860 may compare the standard exercise model of the user class and the user's exercise data to generate a personalized exercise model including the difference value thereof.

The exemplary embodiment of this disclosure can be implemented by various methods. For example, the exemplary embodiment of the present disclosure can be implemented by using hardware, software or its combination. When they are implemented by software, they may be implemented as software executing in more than one processors using various operating systems or platforms. In addition, the software may be created by using any language among various appropriate programming languages or be compiled in machine language codes or intermediate codes executable in a framework or virtual machine.

In addition, when the exemplary embodiment of the present disclosure is executed in more than one processors, the exemplary embodiment of the present disclosure may be implemented by processor readable media such as a memory, a floppy disk, a hard disk, a compact disk (CD), an optical disk or a magnetic tape, or the like in which more than one programs are recorded to conduct the implementation of various exemplary embodiments of the present disclosure.

What is claimed is:

1. A personalized exercise service providing apparatus comprising:
   one or more processors that process computer executable program code embodied in non-transitory computer readable storage media, the computer executable program code comprising:

a user class identifier that identifies a user class of a user based on user data;
an exercise data acquirer that acquires exercise data of the user; and
a model generator that generates a personalized exercise model of the user based on a standard exercise model and the acquired exercise data of the user, and
an image processor that recognizes an image that is obtained by using a plurality of visual sensors are arranged around the user,
wherein the standard exercise model corresponds to the determined user class,
wherein the user data and the exercise data of the user are acquired by the visual sensors,
wherein the exercise data include at least one of exercise posture and exercise pattern of a user,
wherein the user class identifier identifies the user class based on image recognition result received from the image processor and a pre-established database,
wherein the image processor detects a body region of the user from the image that is obtained by at least one of visual sensor of the plurality of visual sensors arranged around the user, extracts body feature points from the detected body region, and provides information of the extracted body feature points to the user class identifier and the exercise data acquirer as the image recognition result,
wherein the body feature points include shoulders, arms, legs and joints of a user, and
wherein, based on the image recognition result received from the image processor based on the image obtained by the at least one visual sensor, the user class identifier identifies a body type of the user and the exercise data acquirer acquires user's exercise data.

2. The apparatus of claim 1, wherein the user class is classified based on at least one of sex, age, and body type comprised in the user data.

3. The apparatus of claim 1, wherein the pre-established database comprises at least one of a feature vector for each user class and information of body feature points for each user class.

4. The apparatus of claim 1, wherein the image processor detects a face region of the user from the image that is obtained by a visual sensor of the plurality of visual sensors, extracts at least one of a feature vector for sex identification and a feature vector for age identification from the detected face region, and provides the at least one extracted feature vector to the user class identifier as the image recognition result,
wherein the user class identifier identifies at least one of sex and age of the user based on the image recognition result received from the image processor based on the image obtained by the visual sensor.

5. The apparatus of claim 1, further comprising equipment controller that controls exercise equipment based on the identified body type of the user or provides exercise equipment information to the user.

6. The apparatus of claim 1, further comprising image processor that recognizes an image that is obtained by a visual sensor,
wherein the exercise data acquirer acquires the exercise data of the user by analyzing the image recognition result received from the image processor.

7. The apparatus of claim 1, wherein the model generator compares exercise data of the standard exercise model corresponding to the user class with the acquired exercise data to generate the personalized exercise model comprising the difference thereof.

8. The apparatus of claim 1, wherein the model generator builds a database for generating exercise models corresponding to each user class by using exercise data of the user and other users and generates the standard exercise model corresponding to each user class based on the built database for generating exercise models.

9. A personalized exercise service providing method comprising:
processing computer executable program code embodied in non-transitory computer readable storage media by one or more processors, the computer executable program code comprising:
determining a user class of a user based on user data;
acquiring exercise data of the user;
generating a personalized exercise model of the user based on a standard exercise model and the acquired exercise data of the user,
acquiring an image of the user;
recognizing the image; and
identifying the user class based on the image recognition result and a pre-established database,
wherein the standard exercise model corresponds to the determined user class,
wherein the user data and the exercise data of the user are acquired by using a plurality of visual sensors are arranged around the user,
wherein the exercise data include at least one of exercise posture and exercise pattern of a user,
wherein the recognizing the image comprising detecting a body region of the user from the image that is obtained by at least one of visual sensor of the plurality of visual sensors arranged around the user, and extracting body feature points from the detected body region,
wherein the body feature points include shoulders, arms, legs and joints of a user, and
wherein, based on information of the extracted body feature points, the identifying the user class identifies a body type of the user, and the acquiring the exercise data acquires exercise data of the user.

10. The method of claim 9, wherein the user class is classified based on at least one of sex, age, and body type comprised in the user data.

11. The method of claim 9, wherein the pre-established database comprises at least one of a feature vector for each user class and information of body feature points for each user class.

12. The method of claim 9, wherein recognizing the image comprises detecting a face region of the user from the image that is obtained by a visual sensor of the plurality of visual sensors, and extracting at least one of a feature vector for sex identification and a feature vector for age identification from the detected face region, and
wherein identifying the user class comprises identifying at least one of sex and age of the user based on the at least one extracted feature vector.

13. The method of claim 9, further comprising a step of controlling exercise equipment based on the identified body type of the user or providing exercise equipment information to the user.

14. The method of claim 9, wherein the acquiring exercise data of the user comprises:
acquiring an image of the user;
recognizing the image of the user; and acquiring the exercise data of the user by analyzing the image recognition result.

15. The method of claim 9, wherein generating a personalized exercise model comprises comparing exercise data of the standard exercise model corresponding to the user class with the acquired exercise data to generate the personalized exercise model comprising the difference thereof.

16. The method of claim 9, further comprising:
building a database for generating exercise models corresponding to each user class by using exercise data of the user and other users; and
generating the standard exercise model corresponding to each user class based on the built database for generating exercise models.

* * * * *